(12) United States Patent
Mori et al.

(10) Patent No.: US 8,663,910 B2
(45) Date of Patent: Mar. 4, 2014

(54) ASSAY METHOD

(75) Inventors: Mikinaga Mori, Kanagawa-ken (JP); Junichi Katada, Kanagawa-ken (JP); Hiroyuki Chiku, Kanagawa-ken (JP); Takayoshi Oyamada, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 815 days.

(21) Appl. No.: 12/562,885

(22) Filed: Sep. 18, 2009

(65) Prior Publication Data
US 2010/0075440 A1 Mar. 25, 2010

(30) Foreign Application Priority Data

Sep. 19, 2008 (JP) ................................. 2008-240201

(51) Int. Cl.
*C12Q 1/00* (2006.01)

(52) U.S. Cl.
USPC ................ 435/4; 435/6.1; 435/7.1; 435/7.93; 435/7.95; 435/960; 436/524

(58) Field of Classification Search
USPC ................ 435/7.1, 7.93, 7.95, 960, 4, 6.1; 436/524
See application file for complete search history.

(56) References Cited

U.S. PATENT DOCUMENTS

| | | | | |
|---|---|---|---|---|
| 4,855,240 A | * | 8/1989 | Rosenstein et al. | 436/514 |
| 4,916,056 A | * | 4/1990 | Brown et al. | 435/7.92 |
| 4,960,691 A | * | 10/1990 | Gordon et al. | 435/6.12 |
| 5,091,153 A | * | 2/1992 | Bachand | 422/411 |
| 5,658,801 A | * | 8/1997 | Poissant et al. | 436/518 |
| 5,660,993 A | * | 8/1997 | Cathey et al. | 435/7.9 |
| 5,798,215 A | * | 8/1998 | Cathey et al. | 435/7.9 |
| 7,189,522 B2 | * | 3/2007 | Esfandiari | 435/7.1 |
| 7,300,802 B2 | * | 11/2007 | Paek et al. | 436/514 |
| 7,682,801 B2 | * | 3/2010 | Esfandiari | 435/7.1 |
| 7,879,597 B2 | * | 2/2011 | Esfandiari | 435/287.2 |
| 7,998,753 B2 | * | 8/2011 | Chiku et al. | 436/514 |
| 2003/0143639 A1 | * | 7/2003 | Matsushita et al. | 435/7.9 |

(Continued)

FOREIGN PATENT DOCUMENTS

| | | |
|---|---|---|
| JP | 2001-004628 A | 1/2001 |
| JP | 2002202307 A * | 7/2002 |
| WO | WO-93/03176 A1 | 2/1993 |

OTHER PUBLICATIONS

Tanaka et al., "Dyeing Utilizing A H2O2-POD System", Clinical Examination, vol. 41 No. 9, Sep. 1997, pp. 1020-1024.

(Continued)

*Primary Examiner* — Melanie Y Brown
*Assistant Examiner* — Erik B Crawford
(74) *Attorney, Agent, or Firm* — Birch, Stewart, Kolasch & Birch, LLP (57) ABSTRACT

A plurality of kinds of liquids, which are of at least three kinds, containing (a) a test body solution containing at least one kind of an analyte, and (b) at least two kinds of liquids selected from the group consisting of a reagent solution, an amplifying solution, and a detecting solution, are fed to a detection site containing a specific binding substance with respect to the analyte. A qualitative analysis or a quantitative analysis of the analyte contained in the test body solution is thereby performed. Directions of liquid feeding of all of the plurality of the kinds of the liquids vary from one another, and the plurality of the kinds of the liquids are caused to intersect with one another at the detection site.

2 Claims, 2 Drawing Sheets

(56) References Cited

U.S. PATENT DOCUMENTS

2008/0318341 A1* 12/2008 Esfandiari .................... 436/518
2010/0261286 A1* 10/2010 Kim et al. .................... 436/149

OTHER PUBLICATIONS

Japanese Office Action issued Mar. 13, 2012, Application No. 2008-240201.

* cited by examiner

ASSAY METHOD

BACKGROUND OF THE INVENTION

1. Field of the Invention

This invention relates to an assay method for performing a qualitative analysis or a quantitative analysis of a sample, which contains an analyte (i.e., a substance to be analyzed), with a high sensitivity.

2. Description of the Related Art

Recently, there have been proposed various simple devices for developing test body solutions and detecting analytes contained in the test body solutions, and various kinds of devices for detection of external diagnostic medicines, poisons, and the like, are available commercially. Examples of the aforesaid devices include the devices utilizing immunochromatographic techniques. With the immunochromatographic techniques, large scale facilities and equipment are not required for making judgments and analyses, and operations are easy to perform. Specifically, in the cases of the immunochromatographic techniques, the results of the analyses are obtained with processing wherein, after a test body solution having the possibility of containing an analyte has been spotted onto a support, the test body solution having been spotted is merely allowed to stand for a period of time falling within the range of approximately 5 minutes to approximately 10 minutes. Therefore, the immunochromatographic techniques have widely been used as the judgment or analysis techniques, which are simple and quick and have high specificity, in a wide variety of use applications, such as clinical examinations in hospitals and assay tests in research laboratories.

Ordinarily, physiologically active substances or environmental pollution substances, such as natural substances, toxins, hormones, or agricultural chemicals, act upon organisms only with markedly small quantities which are not capable of being detected with the conventional ordinary immunochromatographic techniques. Therefore, nowadays there is a strong demand for an immunochromatographic technique with which the aforesaid substances are analyzed quickly, in a simple manner, and with a high sensitivity. Accordingly, besides the immunochromatographic techniques having the simple processing for spotting a test body solution, which contains an analyte, onto a support, and thereby detecting the analyte, for example, there have been used the immunochromatographic techniques wherein, after a test body solution containing an analyte has been spotted onto a support, and the analyte has thus been fixed to the support, the support is washed with a washing liquid, wherein a reaction substrate liquid, an amplifying solution, or the like, is brought into contact with the analyte having thus been fixed, and wherein a signal obtained from the analyte is thus amplified and detected.

As an example of the immunochromatographic technique having a high sensitivity as described above, an immunochromatographic technique is disclosed in, for example, International Patent Publication No. WO93/03176. The disclosed immunochromatographic technique comprises the steps of: causing a test body solution, which contains an analyte and has been brought into contact with an enzyme-labeled antibody, to flow with respect to a solid phase support, to which an analyte capturing reagent has been bound, the analyte-enzyme-labeled antibody complex being thereby bound onto the support, causing a washing liquid and an enzyme substrate liquid to flow in a direction reverse to the direction of the flow of the test body solution, an analyte-enzyme-labeled antibody-enzyme substrate complex being thereby formed, detecting a signal, such as coloring, occurring due to the enzyme substrate, and thereby analyzing the analyte.

With the immunochromatographic technique disclosed in International Patent Publication No. WO93/03176, the signal obtained from the analyte is amplified by the enzyme substrate. Also, by the reversible flow performed such that the washing liquid and the enzyme substrate liquid are caused to flow in the direction reverse to the direction of the flow of the test body solution, the contact of the analyte capturing reagent, which has been bound to the support, and the analyte-enzyme-labeled antibody complex with each other is enhanced. Therefore, the analysis is capable of being made with respect to the trace quantity of the analyte.

However, with the immunochromatographic technique disclosed in International Patent Publication No. WO93/03176, wherein the washing liquid is caused to flow over the entire area of the flow path through which the test body solution has flowed, the problems arise in that a large quantity of the washing liquid is necessary in order for a sufficient washing effect to be obtained. Also, the washing liquid and the enzyme substrate liquid are caused to flow in the direction reverse to the direction of the flow of the test body solution, i.e., from the downstream side with respect to the flow of the test body solution. Therefore, an unbound enzyme-labeled antibody and an unbound analyte, which have not been bound with the analyte capturing reagent on the support, are caused by the washing liquid and the enzyme substrate liquid to flow again on the support. Accordingly, limitation is imposed upon the detection with a high accuracy and a high sensitivity.

SUMMARY OF THE INVENTION

The primary object of the present invention is to provide an assay method, wherein particular contamination is not caused by a washing operation to occur, wherein a sufficient washing effect is obtained with a small quantity of a washing liquid, and wherein analysis is made with a high accuracy and a high sensitivity.

The present invention provides an assay method, comprising:

i) preparing a plurality of kinds of liquids, which are of at least three kinds, containing:
  a) a test body solution containing at least one kind of an analyte, and
  b) at least two kinds of liquids selected from the group consisting of a reagent solution, an amplifying solution, and a detecting solution, and ii) feeding the plurality of the kinds of the liquids to a detection site containing a specific binding substance with respect to the analyte, whereby a qualitative analysis or a quantitative analysis of the analyte contained in the test body solution is performed, wherein directions of liquid feeding of all of the plurality of the kinds of the liquids vary from one another, and the plurality of the kinds of the liquids are caused to intersect with one another at the detection site.

The term "reagent solution" as used herein means the solution containing a chemical agent having a role supplementary to the amplifying solution or the detecting solution and also means the liquid having the washing function in the assay processing. The term "amplifying solution" as used herein means the solution containing a chemical agent, which is caused by the effect of the labeling substance or the analyte to undergo a catalytic reaction for yielding a colored compound, light emission, or the like, and thereby producing signal amplification. The term "detecting solution" as used herein means the solution containing a chemical agent, which undergoes a reaction with the labeling substance, the analyte, or the like, to form a discolored compound or a colored compound, or to produce an alteration, such as light emission.

The assay method in accordance with the present invention may be applied to processing utilizing specific binding as in the cases of an antigen-antibody reaction, such as DNA hybridization or binding of an aptamer with a specific protein. In cases where the analyte contained in the test body solution is an enzyme, the assay method in accordance with the present invention may be applied to detection wherein a reaction substrate is caused to produce a color by the catalytic effect of the enzyme. The assay method in accordance with the present invention may also be applied to biochemical examinations wherein the analyte is detected as the substrate.

The assay method in accordance with the present invention should preferably be modified such that the detection site is formed on an insoluble support, and the liquid feeding is performed by capillary force arising through the insoluble support.

Also, the assay method in accordance with the present invention should preferably be modified such that a labeling substance signal, which is obtained from a labeling substance complex having been modified by a substance that has capability of binding with the analyte or the specific binding substance, is detected.

Further, the assay method in accordance with the present invention should preferably be modified such that the plurality of the kinds of the liquids contain the amplifying solution, and the labeling substance signal, which is obtained from the labeling substance complex and which has been amplified by the liquid feeding of the amplifying solution, is detected.

Furthermore, the assay method in accordance with the present invention should preferably be modified such that the plurality of the kinds of the liquids contain the test body solution, the reagent solution, the amplifying solution, and the detecting solution, the test body solution is fed to the insoluble support that is provided with the detection site, each of a liquid feeding insoluble support for liquid feeding of the reagent solution and an absorbing insoluble support for absorption of the reagent solution is brought into contact with the insoluble support that is provided with the detection site, the reagent solution is fed for washing off substances other than the labeling substance which has been specifically bound with the detection site on the insoluble support that is provided with the detection site, and the amplifying solution and the detecting solution are fed to the intersection site, at which the test body solution and the reagent solution intersect with each other.

Also, the assay method in accordance with the present invention should preferably be modified such that the insoluble support that is provided with the detection site has a strip-like shape, and the direction of the liquid feeding of the amplifying solution is normal to a principal plane of the insoluble support that is provided with the detection site.

Further, the assay method in accordance with the present invention should preferably be modified such that the labeling substance is constituted of a substance containing fine metal particles.

In such cases, the assay method in accordance with the present invention should preferably be modified such that the amplifying solution is a liquid containing silver ions.

Also, the assay method in accordance with the present invention should preferably be modified such that a liquid containing a reducing agent for the silver ions contained in the amplifying solution is used as the reagent solution.

The assay method in accordance with the present invention comprises:

i) preparing the plurality of the kinds of the liquids, which are of at least three kinds, containing:

a) the test body solution containing at least one kind of the analyte, and b) at least two kinds of the liquids selected from the group consisting of the reagent solution, the amplifying solution, and the detecting solution, and ii) feeding the plurality of the kinds of the liquids to the detection site containing the specific binding substance with respect to the analyte, whereby the qualitative analysis or the quantitative analysis of the analyte contained in the test body solution is performed, wherein the directions of the liquid feeding of all of the plurality of the kinds of the liquids vary from one another, and the plurality of the kinds of the liquids are caused to intersect with one another at the detection site.

Therefore, with the assay method in accordance with the present invention, the site of the intersection of the flow paths of the plurality of the kinds of the liquids, which are of at least three kinds, is limited to the detection site.

Accordingly, for example, there is no risk that the unbound analyte and impurities contained in the test body solution, which have been accumulated on the side downstream with respect to the liquid feeding direction due to the liquid feeding of the test body solution, will again flow to the detection site. Therefore, a large quantity of the reagent solution need not be used, and the washing of the detection site is performed efficiently. As a result, the detection is performed with a high accuracy. Also, with respect to the analyte which is contained in the test body solution and which has not been bound with the labeling substance, the efficiency of the binding with the specific binding substance contained at the detection site is enhanced. Accordingly, the efficiency of the ultimate sandwich binding is enhanced, and the detection is performed with a high sensitivity.

Particularly, in cases where the plurality of the kinds of the liquids, which are of at least three kinds, contain the amplifying solution, the labeling substance signal, which is obtained from the labeling substance complex having been modified by the substance that has the capability of binding with the analyte or the specific binding substance, is amplified by the liquid feeding of the amplifying solution. Therefore, the reversible flowing of the test body solution for enhancing the contact of the analyte with the specific binding substance need not be performed, and the detection is performed with a high sensitivity.

The present invention will hereinbelow be described in further detail with reference to the accompanying drawings.

DETAILED DESCRIPTION OF THE INVENTION

Figure 1:
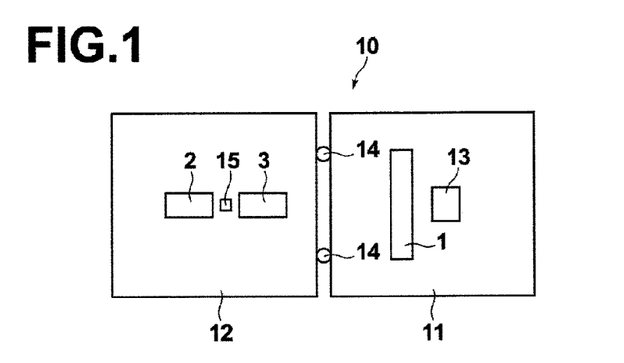
FIG. 1 is an explanatory exploded view showing an immunochromatographic kit, which may be used in an embodiment of the assay method in accordance with the present invention.
Figure 2:
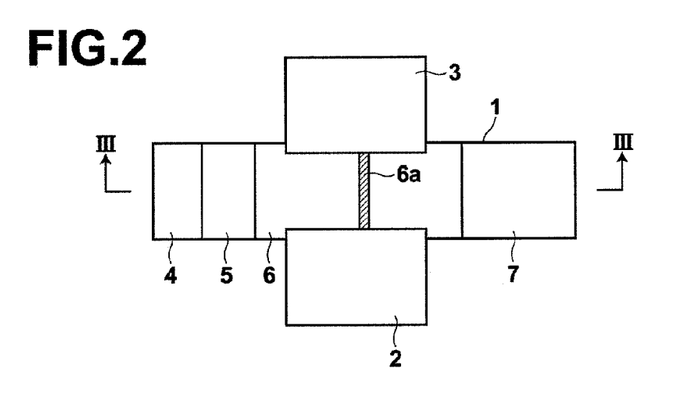
FIG. 2 is an explanatory plan view showing the state of contact of an immunochromatographic strip with each of a liquid feeding insoluble support and an absorbing insoluble support.
Figure 3:
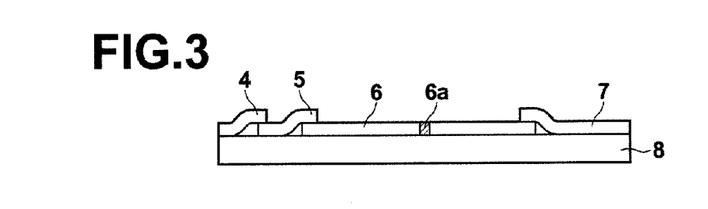
FIG. 3 is a sectional view taken online of FIG. 2, and FIGS. 4A, 4B, and 4C are explanatory plan views showing a procedure in the embodiment of the assay method in accordance with the present invention.

An embodiment of the assay method in accordance with the present invention will hereinbelow be described with reference to the accompanying drawings. FIG. 1 is an explanatory exploded view showing an immunochromatographic kit, which may be used in an immunoassay method (an immunological assay method) acting as an embodiment of the assay method in accordance with the present invention. FIG. 2 is an explanatory plan view showing the state of contact of an immunochromatographic strip with each of a liquid feeding insoluble support and an absorbing insoluble support. FIG. 3 is a sectional view taken on line of FIG. 2.

With reference to FIG. 1, an immunochromatographic kit 10 comprises a first device part 11 for supporting an immunochromatographic strip (acting as an insoluble support) 1. The immunochromatographic kit 10 also comprises a second device part 12 for supporting a liquid feeding insoluble support 2 and an absorbing insoluble support 3. The first device part 11 and the second device part 12 are connected with each other by position adjusting members 14, 14. The position adjusting members 14, 14 secure the first device part 11 and the second device part 12 in a state in which the immunochromatographic strip 1 is not in contact with each of the liquid feeding insoluble support 2 and the absorbing insoluble support 3. Also, the position adjusting members 14, 14 secure the first device part 11 and the second device part 12 such that, at the time at which the first device part 11 and the second device part 12 have been closed so as to stand facing each other, the immunochromatographic strip 1 supported by the first device part 11 comes into contact with each of the liquid feeding insoluble support 2 and the absorbing insoluble support 3, which are supported by the second device part 12, as illustrated in FIG. 2.

The first device part 11 is provided with a liquid storing pot 13 for loading of a liquid. The liquid storing pot 13 is formed such that, in cases where the first device part 11 and the second device part 12 are adjusted and secured at the positions at which the immunochromatographic strip 1 comes into contact with each of the liquid feeding insoluble support 2 and the absorbing insoluble support 3, an edge of the liquid feeding insoluble support 2 may be dipped in the liquid storing pot 13.

Also, a spotting hole 15 is located between the liquid feeding insoluble support 2 and the absorbing insoluble support 3, which are supported by the second device part 12. In cases where the first device part 11 and the second device part 12 are adjusted and secured at the positions at which the immunochromatographic strip 1 comes into contact with each of the liquid feeding insoluble support 2 and the absorbing insoluble support 3, the spotting hole 15 is used for spotting a liquid from the side of the rear surface of the second device part 12 onto the immunochromatographic strip 1.

As illustrated in FIG. 2 and FIG. 3, the immunochromatographic strip 1 comprises a sample adding pad 4, to which the test body solution is to be spotted. The immunochromatographic strip 1 also comprises a labeling substance supporting pad 5, to which the labeling substance having the capability of binding with the analyte or the specific binding substance has been fixed. The immunochromatographic strip 1 further comprises a chromatographic support 6, which is provided with a detection line (detection site) 6a containing the specific binding substance with respect to the analyte. The immunochromatographic strip 1 still further comprises an absorbing pad 7 for absorbing the test body solution having been fed. The sample adding pad 4, the labeling substance supporting pad 5, the chromatographic support 6, and the absorbing pad 7 are located on an adhesive sheet 8. As an aid in facilitating the explanation, in this embodiment, only one detection line 6a is formed as the detection site. Alternatively, a plurality of detection lines containing different specific binding substances may be formed. With the constitution provided with the plurality of the detection lines, in cases where a plurality of analytes are contained in the test body solution, the plurality of the analytes may be detected with one time of processing. Also, if necessary, the chromatographic support 6 may be provided with a region (i.e., a control site), to which a specific binding substance for control has been fixed.

Figure 4A:
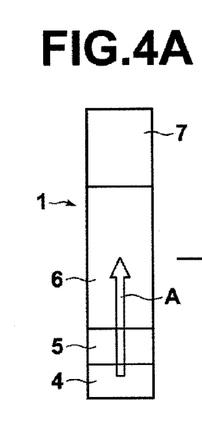

A procedure in the embodiment of the assay method in accordance with the present invention will be described hereinbelow with reference to FIGS. 4A, 4B, and 4C. In this embodiment, by way of example, the test body solution, the washing liquid acting as the reagent solution, and the amplifying solution are used as the plurality of the kinds of the liquids. Firstly, as illustrated in FIG. 4A, the test body solution is spotted onto the sample adding pad 4 of the immunochromatographic strip 1. The test body solution having thus been spotted is fed in the direction indicated by the arrow A by the capillary force arising through the immunochromatographic strip 1. The labeling substance supporting pad 5 contains the labeling substance having the capability of binding with the analyte. Therefore, the analyte contained in the test body solution is labeled with the labeling substance, while the test body solution is being fed in the direction indicated by the arrow A through the labeling substance supporting pad 5.

The analyte having thus been labeled with the labeling substance is caused to migrate even further in the direction indicated by the arrow A by the capillary force arising through the immunochromatographic strip 1 and is captured by the detection line 6a that is the region to which the specific binding substance has been fixed. Specifically, at the detection line 6a, a specific binding substance-analyte-labeling substance complex is formed. The analyte, which has not been captured, the unreacted labeling substance, which has not been bound, and the like, are absorbed by the absorbing pad 7. At the stage of the liquid feeding of the test body solution as illustrated in FIG. 4A, the first device part 11 and the second device part 12 are secured by the position adjusting members 14, 14 in the state in which the immunochromatographic strip 1 is not in contact with each of the liquid feeding insoluble support 2 and the absorbing insoluble support 3.

In this embodiment, the analyte contained in the test body solution is bound with the labeling substance contained in the labeling substance supporting pad 5. Alternatively, the labeling substance may be of the type bound with the specific binding substance having been fixed to the detection line 6a. In such cases, a specific binding substance-labeling substance-analyte complex is formed at the detection line 6a.

Figure 4B:
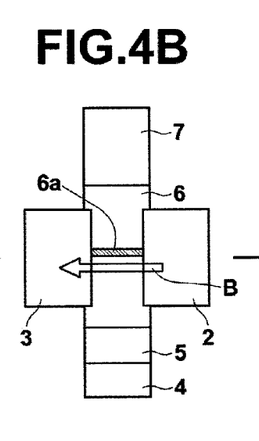

Thereafter, as illustrated in FIG. 4B, the unreacted labeling substance, or the like, which remains without undergoing the specific binding reaction at the detection line 6a of the chromatographic support 6, is washed off. In the washing process, the first device part 11 and the second device part 12 are closed so as to stand facing each other. Also, the first device part 11 and the second device part 12 are secured by the position adjusting members 14, 14, such that a part of the liquid feeding insoluble support 2 and a part of the absorbing insoluble support 3 come into contact with the edges of the chromatographic support 6 of the immunochromatographic strip 1, which has the strip-like shape.

At this time, an edge of the liquid feeding insoluble support 2 is dipped in the liquid storing pot 13 of the first device part 11. Also, the washing liquid is fed by the capillary force of the liquid feeding insoluble support 2 from the liquid feeding insoluble support 2 toward the absorbing insoluble support 3 (i.e., in the direction indicated by the arrow B in FIG. 4B). Specifically, the liquid feeding is performed such that the direction of the liquid feeding of the test body solution (i.e., the direction indicated by the arrow A) and the direction of the liquid feeding of the washing liquid (i.e., the direction indicated by the arrow B) intersect with each other at the detection line 6a. In cases where the liquid feeding is performed in the manner described above, the joining of the flow path of the test body solution (i.e., the flow path through the immunochromatographic strip 1) and the flow path of the washing liquid (i.e., the flow path from the liquid feeding insoluble support 2 to the absorbing insoluble support 3) with each other is minimized. Further, since the detection of the analyte is made at the detection line 6a, in cases where the chromatographic support 6 containing the detection line 6a is washed with the washing liquid, the substances other than the labeling substance having been specifically bound at the detection line 6a are washed off sufficiently even with a small quantity of the washing liquid.

If the direction of the liquid feeding of the test body solution and the direction of the liquid feeding of the washing liquid are identical with each other (i.e., if both of the direction of the liquid feeding of the test body solution and the direction of the liquid feeding of the washing liquid coincide with the direction indicated by the arrow A), the labeling substance contained in the labeling substance supporting pad 5 will be caused by the washing liquid to flow out, and the unbound labeling substance will cling to the detection line 6a. In such cases, even if the chromatographic support 6 is provided with the control site, the problems will occur in that the intensity of the background will become high, and the accuracy of the analysis will not be kept high. Also, in order for the aforesaid problems to be eliminated, it is necessary to perform the washing with a large quantity of the washing liquid. However, in such cases, the problems will occur in that a variation inaccuracy will arise in accordance with the quantity of the washing liquid used, and the specific binding substance-analyte-labeling substance complex having been bound with the detection line 6a will flow out together with the washing liquid.

Further, if the direction of the liquid feeding of the test body solution and the direction of the liquid feeding of the washing liquid are reverse to each other, the analyte, which has not been captured and which has been absorbed by the absorbing pad 7, and the unreacted labeling substance, which has not undergone the binding and which has been absorbed by the absorbing pad 7, will flow out from the absorbing pad 7 and will cling to the detection line 6a. In such cases, the problems will occur in that the accuracy of the analysis is not kept high, and it is necessary for the washing to be performed with a large quantity of the washing liquid.

As described above, with the assay method in accordance with the present invention, the joining of the flow path of the test body solution (i.e., the flow path through the immunochromatographic strip 1) and the flow path of the washing liquid (i.e., the flow path from the liquid feeding insoluble support 2 to the absorbing insoluble support 3) with each other is minimized. Therefore, there is no risk that the unbound analyte and impurities contained in the test body solution, which have been accumulated on the side downstream with respect to the liquid feeding direction due to the liquid feeding of the test body solution, will again flow to the detection site. Therefore, a large quantity of the washing liquid need not be used, and the washing of the detection site is performed efficiently. As a result, the detection is performed with a high accuracy.

Figure 4C:
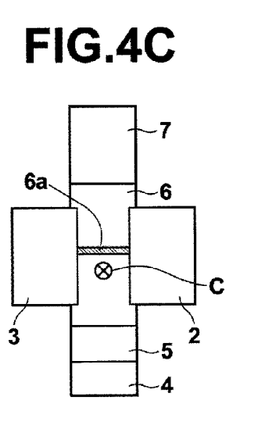

Thereafter, as illustrated in FIG. 4C, the amplifying solution is fed from the spotting hole 15, which is formed through the second device part 12, to the detection line 6a. The amplifying solution is fed in the direction (indicated by the arrow C in FIG. 4C) normal to plane of the sheet of FIG. 4C, i.e., from above the detection line 6a. In cases where the amplifying solution is fed in the manner described above, the quantity of the amplifying solution required is kept small, and amplification non-uniformity is suppressed. After the amplifying solution has been fed, the liquid feeding insoluble support 2 and the absorbing insoluble support 3 are separated from the immunochromatographic strip 1. In this manner, the qualitative analysis or the quantitative analysis is performed easily.

In the embodiment described above, the direction of the liquid feeding of the test body solution (i.e., the direction indicated by the arrow A), the direction of the liquid feeding of the washing liquid (i.e., the direction indicated by the arrow B), and the direction of the liquid feeding of the amplifying solution (i.e., the direction indicated by the arrow C), are normal to one another. However, the directions of the liquid feeding are not limited to the directions normal to one another. It is sufficient for the directions of the liquid feeding to be set such that the directions of the liquid feeding intersect with one another at the detection line 6a. Also, in the embodiment described above, the three kinds of the liquids, i.e. the test body solution, the washing liquid (acting as the reagent solution), and the amplifying solution, are employed as the plurality of the kinds of the liquids. Alternatively, the plurality of the kinds of the liquids may be of a different combination of the liquids, which contain the test body solution. For example, the plurality of the kinds of the liquids may be of a combination of the test body solution, the amplifying solution, and the detecting solution. As another example, the plurality of the kinds of the liquids may be of a combination of the test body solution, the reagent solution, and the detecting solution.

Further, in the embodiment described above, the detection site is formed on the insoluble support, and the liquid feeding is performed by the capillary force arising through the insoluble support. However, the assay method in accordance with the present invention is also applicable to an assay technique in which the insoluble support is not employed. For example, the assay method in accordance with the present invention may be applied to an assay technique employing a micro liquid chip constituted of a plastic base plate on which grooves acting as flow paths have been engraved, wherein the flow paths are located in a three-dimensional pattern, wherein the directions of the liquid feeding of all of the plurality of the kinds of the liquids vary from one another, and wherein a detection site is formed at a point of intersection of the flow path.

Various kinds of the solutions, such as the test body solution and the reagent solution, the labeling substance, the insoluble support, and the like, which may be employed in the assay method in accordance with the present invention, will be described hereinbelow.

[Test Body Solution]

The test body solution to be analyzed by the assay method in accordance with the present invention may be selected from a wide variety of solutions having the possibility of containing analytes (for example, physiologically active substances or environmental pollution substances, such as natural substances, toxins, hormones, or agricultural chemicals). For example, the test body solution may be one of various biological samples. Particularly, the biological sample may be a humor of an animal (particularly, a human), such as blood, blood serum, blood plasma, a marrow liquid, a tear liquid, sweat, urine, pus, a nose liquid, or sputum; excrement, such as fecal matter; an internal organ; a tissue; a mucous membrane or a skin; a scrubbed test body (a swab) presumed to contain the mucous membrane or the skin; a mouth rinsing liquid; an animal or a vegetable itself; or a diluted sample of a dried animal body or a dried vegetable body having been diluted with a diluting liquid, which will be described later.

The test body solution described above may be used directly in the form of the test body solution. Alternatively, the test body solution may be used in the form of an extract liquid, which is obtained from the extraction processing performed on the test body solution by use an appropriate extraction solvent. As another alternative, the test body solution may be used in the form of a diluted liquid, which is obtained by diluting the extract liquid by use of an appropriate diluent. As a further alternative, the test body solution may be used in the form of a concentrated liquid, which is obtained by concentrating the extract liquid with an appropriate technique. As the extraction solvent, it is possible to use a solvent which is used in the ordinary immunological analysis techniques (such as water, physiological saline, or a buffer solution), or a water-miscible organic solvent which is adapted for performing a direct specific binding reaction (e.g., an antigen-antibody reaction) by being diluted with the solvent described above.

[Labeling Substance]

The labeling substance which may be used in the assay method in accordance with the present invention may be selected from a wide variety of labeling substances which are perceptible as colors or are detectable with a reaction, e.g., fine metal particles, colored latex particles, or enzymes, such as those employed in the ordinary immunochromatographic techniques. In cases where the signal is to be amplified by deposition of a metal to the labeling substance through a reducing reaction of the metal ions utilizing the labeling substance as a catalyst, from the view point of the catalytic activity, the leveling substance should preferably be the fine metal particles.

As the fine metal particles, it is possible to use a metal colloid, a metal sulfide, a metal alloy, or a polymer particle label containing a metal. The mean particle diameter of the particles (or the colloidal particles) should preferably fall within the range of 0.02 µm to 10 µm. Examples of the fine metal particles include a gold colloid, a silver colloid, a platinum colloid, an iron colloid, an aluminum hydroxide colloid, and a composite colloid constituted of two or more of the above-enumerated colloids. The fine metal particles should preferably be the gold colloid, the silver colloid, the platinum colloid, or the composite colloid constituted of two or more of the above-enumerated colloids. From the view point of the perceptibility, the fine metal particles should more preferably be the gold colloid, which has a red color in the cases of an appropriate particle diameter range, or the silver colloid, which has a yellow color in the cases of an appropriate particle diameter range. The mean particle diameter of the metal colloid should preferably fall within the range of approximately 1 nm to approximately 500 nm, and should more preferably fall within the range of 1 nm to 50 nm.

[Specific Binding Substance]

The specific binding substance may be selected from a wide variety of substances which have affinity with respect to the analyte. For example, the specific binding substance may be an antibody. For example, as the specific binding substance, it is possible to employ an antiserum, which is prepared from a blood serum of an animal having been immunized by the analyte, an immunoglobulin fraction, which has been purified from the antiserum, a monoclonal antibody, which is obtained from cell fusion using spleen cells of an animal having been immunized by the analyte, or a fragment of the above-enumerated substances (e.g., F(ab')$_2$, Fab, Fab', or Fv). The above-enumerated antibodies may be prepared in accordance with the conventional procedures.

[Amplification of Signal of Labeling Substance]

In cases where a metal colloid label, a metal sulfide label, a metal alloy label, or a polymer particle label containing a metal is used as the labeling substance, the signal of the metal type label may be amplified. Specifically, after the complex of the analyte and the labeling substance has been formed, silver ions, which are supplied by a silver-containing compound, such as an inorganic silver salt or an organic silver salt, and a reducing agent may be brought into contact with each other, and the silver ions may thus be reduced by the reducing agent to form silver particles. The silver particles having thus been formed may be deposited on the metal type label with the metal type label acting as the nucleus. As a result, the signal obtained from the metal type label is amplified, and the analysis of the analyte is made with a high sensitivity.

[Immunochromatographic Strip (insoluble Support)]

As illustrated in FIG. 2 and FIG. 3, the immunochromatographic strip 1 is the support provided with at least one detection line 6a containing the specific binding substance having the capability of binding with the analyte. The immunochromatographic strip 1 is partitioned into the sample adding pad 4, the labeling substance supporting pad 5, the chromatographic support 6, and the absorbing pad 7. The sample adding pad 4, the labeling substance supporting pad 5, the chromatographic support 6, and the absorbing pad 7 are located in this order from the upstream side toward the downstream side with respect to the direction of development and are located on the adhesive sheet 8. The immunochromatographic strip 1 should preferably be constituted of a porous material. Examples of the preferable porous materials include a nitrocellulose film, a cellulose film, an acetylcellulose film, a polysulfone film, a polyether sulfone film, a nylon film, glass fibers, a nonwoven fabric, a fabric, and threads. (More preferable materials for each of the pads and the chromatographic support 6 will be described below.)

The chromatographic support 6 is provided with the detection line 6a, to which the specific binding substance with respect to the analyte has been fixed. If necessary, the chromatographic support 6 may also be provided with the control site. The specific binding substance may be directly fixed by the physical or chemical binding to the region of the chromatographic support 6. Alternatively, the specific binding substance may be physically or chemically bound with fine particles, such as latex particles, and the fine particles may then be trapped and fixed to the region of the chromatographic support 6. After the specific binding substance has been fixed to the chromatographic support 6, the chromatographic support 6 should preferably be subjected to non-specific adsorption preventing processing, such as processing with an inactive protein.

The labeling substance supporting pad 5 may be prepared with processing, wherein a suspension containing the labeling substance described above is prepared, coated on an appropriate pad, e.g. a glass fiber pad, and then dried. Examples of the materials for the labeling substance supporting pad 5 include cellulose filter paper, glass fibers, and a nonwoven fabric.

The sample adding pad 4 is the region onto which the test body sample containing the analyte is spotted. The sample adding pad 4 has the function of removing insoluble particles, and the like, from the sample by filtration. Examples of the materials for the sample adding pad 4 include the materials having uniform characteristics, such as cellulose filter paper, glass fibers, a polyurethane, a polyacetate, cellulose acetate, a nylon, and a cotton fabric. If necessary, such that the problems may be prevented from occurring in that, at the time of the analysis, the analyte contained in the sample is adsorbed non-specifically to the material of the sample adding section, and the accuracy of the analysis becomes low, the sample adding pad 4 may be previously subjected to the non-specific adsorption preventing processing.

The absorbing pad 7 is the region for physically absorbing the spotted sample through chromatographic migration. The absorbing pad 7 also absorbs and removes the unreacted labeling substance, or the like, which has not been insolubilized at the detection line 6a of the chromatographic support 6. Examples of the materials for the absorbing pad 7 include water absorbing materials, such as cellulose filter paper, a nonwoven fabric, a fabric, and cellulose acetate. The rate of the chromatographic migration, which occurs after the leading edge part of the chromatographic migration of the spotted sample has reached the absorbing region, varies in accordance with the material of the absorbing region, the size of the absorbing region, and the like. Therefore, by the appropriate selection of the material of the absorbing region, the size of the absorbing region, and the like, the rate adapted for the analysis of the analyte may be set.

[Liquid Feeding Insoluble Support]

The liquid feeding insoluble support 2 may be constituted of one of a wide variety of materials to which the washing liquid is capable of being added. Examples of the materials for the liquid feeding insoluble support 2 include a glass fiber pad, a cellulose membrane, and a nitrocellulose membrane.

[Absorbing Insoluble Support]

The absorbing insoluble support 3 may be constituted of one of a wide variety of materials which are capable of absorbing the washing liquid. Examples of the materials for the absorbing insoluble support 3 include cellulose, nitrocellulose, glass fibers, and a mixture of the above-enumerated materials.

[Reagent Solution]

The term "reagent solution" as used herein means the solution containing the chemical agent having the role supplementary to the amplifying solution or the detecting solution. For example, in cases where the amplifying solution is a silver ion solution as will be described later, the reagent solution may be a hydroquinone solution or a bivalent iron ion solution, acting as a reducing agent with respect to the silver ions. In cases where the amplification with peroxidase enzyme is to be performed, a hydrogen peroxide solution may act as the reagent solution. The reagent solution may also be the washing liquid having the washing function in the assay processing.

The washing liquid may be selected from a wide variety of liquids for washing off the unreacted labeling substance, which remains non-specifically in the chromatographic support 6 without undergoing the specific binding reaction at the detection line 6a of the chromatographic support 6. The washing liquid may be a solvent alone, such as water or ethanol. Alternatively, for example, the washing liquid may be a solution, such as a PBS buffer containing 1% of BSA, or a surface-active agent. Also, as the washing liquid, it is possible to use a liquid containing the silver ions as will be described later, or a liquid containing a reducing agent for the silver ions. Since the washing liquid is developed while it is washing off the unreacted labeling substance, which remains non-specifically in the chromatographic support 6, during the development, the washing liquid is developed while the washing liquid is containing the labeling substance. Therefore, in order for the washing effect to be enhanced, the washing liquid free from the labeling substance is used as the washing liquid before being developed. In order for the washing effect to be enhanced, the pH value of the washing liquid may be adjusted, or a washing liquid containing a surface-active agent constituent, a protein, such as BSA, or a polymer compound, such as a polyethylene glycol, may be used.

[Amplifying Solution]

The amplifying solution is the solution containing the chemical agent, which is caused by the effect of the labeling substance or the analyte to undergo the catalytic reaction for yielding a colored compound, light emission, or the like, and thereby producing signal amplification. For example, the amplifying solution may be a silver ion solution yielding deposition of metallic silver on a metal label through physical development. Alternatively, the amplifying solution may be a solution of a phenylenediamine compound and a naphthol compound having the effect such that a dye is formed by the action of a peroxidase label and hydrogen peroxide.

Specifically, it is possible to use the so-called "developing solution," such as one of those described in ordinary books in the field of the photographic chemistry, e.g. "Kaitei Shashinkogaku No Kiso—Gin-en Shashin Hen" (Revised Edition: Fundamentals of Photographic Engineering—Silver Salt Photograph Edition), edited by The Society of Photographic Science and Technology of Japan, published by Corona Publishing Co., Ltd.; "Shashin No Kagaku" (Photographic Chemistry), Akira Sasai, published by Shashin Kogyo Shuppansha; and "Saishin Shoho Handbook" (Up-To-Date Prescription Handbook), Shin-ichi Kikuchi, et al., published by Amiko Shuppansha. The amplifying solution may be selected from a wide variety of the so-called "physical development solutions" containing silver ions, in which the silver ions are reduced around metal colloids, and the like, acting as development nucleuses.

The compounds containing the silver ions, the reducing agents for the silver ions, and the like, which may be employed for the amplifying solution, will be described hereinbelow.

[Compound Containing Silver Ions]

As the compound containing the silver ions, it is possible to use an organic silver salt, an inorganic silver salt, or a silver complex. The compound containing the silver ions should preferably be selected from the compounds having a high solubility with respect to a solvent, e.g. water. Examples of the compounds described above include silver nitrate, silver acetate, silver lactate, silver butyrate, and silver thiosulfate. Particularly, silver nitrate is preferable. The silver complex should preferably be a silver complex coordinated with a ligand having a water-soluble group, such as a hydroxyl group or a sulf one group. For example, the silver complex should preferably be a hydroxythioether silver complex.

The inorganic silver salt or the silver complex may ordinarily be contained in a proportion on the silver basis falling within the range of 0.001 mol/m$^2$ to 0.2 mol/m$^2$, and should preferably be contained in a proportion on the silver basis falling within the range of 0.01 mol/m$^2$ to 0.05 mol/m$^2$.

[Reducing Agent for Silver Ions]

The reducing agent for the silver ions may be selected from a wide variety of materials, such as inorganic materials, organic materials, and mixtures thereof, which have capability of reducing the silver ions to silver.

Examples of the preferable inorganic reducing agents include a reducing metal salt and a reducing metal complex of metal ions, such as $Fe^{2+}$, $V^{2+}$, or $Ti^{3+}$, whose valence is capable of being altered. In cases where the inorganic reducing agent is used, it is necessary that the oxidized ions are formed into a complex or reduced and are thus removed or rendered harmless. For example, in the system in which $Fe^{2+}$ is used as the reducing agent, $Fe^{3+}$ occurring as the oxide may be formed into a complex by use of citric acid or EDTA and may thus be rendered harmless. In the system of the embodiment, the inorganic reducing agent should preferably be used, and a $Fe^{2+}$ metal salt should more preferably be used.

It is also possible to use a developing agent, which is utilized for a wet type silver halide light-sensitive photographic material, such as methyl gallate, hydroquinone, a substituted hydroquinone, 3-pyrazolidone, p-aminophenol, p-phenylenediamine, a hindered phenol, amidoxime, an azine, catechol, pyrogallol, ascorbic acid (or a derivative thereof), or a leuco-pigment. It is also possible to use one of other materials known to experts in the art, e.g. the materials described in U.S. Pat. No. 6,020,117.

As the reducing agent, the ascorbic acid reducing agent is preferable. Examples of the useful ascorbic acid reducing agents include ascorbic acid, ascorbic acid analogs, ascorbic acid isomers, and derivatives thereof. Specifically, examples of the useful ascorbic acid reducing agents include D- or L-ascorbic acid, a saccharide derivative thereof (e.g., γ-lactascorbic acid, glucoascorbic acid, fucoascorbic acid, glucoheptoascorbic acid, or maltoascorbic acid), a sodium salt of ascorbic acid, a potassium salt of ascorbic acid, isoascorbic acid (or L-erythroascorbic acid), a salt thereof (e.g., an alkali metal salt, an ammonium salt, or a salt known in the art), an enediol type of ascorbic acid, an enaminol type of ascorbic acid, and a thioenol type of ascorbic acid. Particularly, D-, L-, or D,L-ascorbic acid (or an alkali metal salt thereof) or isoascorbic acid (or an alkali metal salt thereof) is preferable. The preferable salt is the sodium salt. If necessary, a mixture of two or more of the above-enumerated reducing agents may be used.

[Dye Amplifying Solution]

For the dye amplifying solution, it is possible to use preferably a color forming substrate for horseradish peroxidase detection as described in, for example a non-patent literature "Dyeing Utilizing a $H_2O_2$-POD System", K. Tanaka and Y. Miki, Clinical Examination, Vol. 41, No. 9, pp. 1020-1024, 1997. A color forming substrate described in Japanese Patent Application 2007-332287 is particularly preferable.

[Detecting Solution]

The term "detecting solution" as used herein means the solution containing the chemical agent, which undergoes the reaction with the labeling substance, the analyte, or the like, to form the discolored compound or the colored compound, or to produce an alteration, such as light emission. Examples of the detecting solutions include o-Cresolphthalein Complexon, which forms a complex with calcium ions acting as the analyte and thereby forms a color, and a copper ion solution, which is discolored through a reaction with a protein acting as the analyte. Examples of the detecting solutions also include solutions of labeled complexes having the capability of undergoing the specific reaction with analytes, such as a labeled DNA or a labeled RNA for detecting DNA or RNA through hybridization, antibody-sensitized particles for detecting an antigen, and an antibody-labeled enzyme.

[Other Auxiliaries]

Examples of other auxiliaries for the amplifying solution often include a buffering agent, an antiseptic agent, e.g. an anti-oxidizing agent or an organic stabilizing agent, and rate regulating agent. As the buffering agent, it is possible to use, for example, a buffering agent utilizing acetic acid or a salt thereof, citric acid or a salt thereof, sodium hydroxide or a salt thereof, or tris(hydroxymethyl)aminomethane. It is also possible to use a buffering agent, which is utilized for ordinary chemical experiments. By appropriate use of the buffering agent, it is possible to adjust the pH value at a value optimum for the amplifying solution. Also, as the additive acting as an anti-fogging agent, it is possible to use an alkyl amine, particularly preferably dodecylamine.

The present invention will further be illustrated by the following non-limitative examples.

EXAMPLES (1) Preparation of Immunochromatographic Strip for Detection of Influenza A Type and B Type
(1-1) Preparation of Gold Colloid Modified by Anti-Influenza A Type and B Type Antibodies
(1-1-1) Preparation of Gold Colloid Modified by Anti-Influenza A Type Antibody Firstly, 1 ml of a 50 mM $KH_2PO_4$ buffer (pH 7.5) was added to 9 ml of a 50 nm-diameter gold colloid solution (EM. GC50, supplied by BBI), and the pH value of the gold colloid solution was thereby adjusted. Thereafter, 1 ml of a 90 µg/ml anti-influenza A type monoclonal antibody (Anti-Influenza A SPTN-5 7307, supplied by Medix Biochemica Oy Ab) solution was added to the gold colloid solution, and the resulting mixture was stirred. After the mixture was allowed to stand for 10 minutes, 550 µl of an aqueous 1% polyethylene glycol (PEG Mw. 20,000, item No. 168-11285, supplied by Wako Pure Chemical Industries, Ltd.) solution was added to the mixture, and the resulting mixture was stirred. Thereafter, 1.1 ml of an aqueous 10% bovine serum albumin (BSA FractionV, item No. A-7906, supplied by Sigma-Aldrich Japan) solution was added to the mixture, and the resulting mixture was stirred. The solution having thus been obtained was subjected to centrifugal processing under the conditions of 8,000×g, 4° C., and 30 minutes (himacCF16RX, supplied by Hitachi, Ltd.). A supernatant liquid was then removed with approximately 1 ml being kept unremoved, and the gold colloid was then subjected to re-dispersing processing by use of an ultrasonic washing machine. Thereafter, the gold colloid was dispersed in 20 ml of a gold colloid storing liquid (20 mM Tris-HCl buffer (pH 8.2), 0.05% PEG (Mw. 20,000), 150 mM NaCl, 1% BSA, 0.1% $NaN_3$). The resulting dispersion was subjected to the centrifugal processing under the conditions of 8,000×g, 4° C., and 30 minutes. A supernatant liquid was then removed with approximately 1 ml being kept unremoved, and the gold colloid was then subjected to the re-dispersing processing by use of the ultrasonic washing machine. In this manner, an antibody-modified gold colloid (50 nm) solution was obtained.

(1-1-2) Preparation of Gold Colloid Modified by Anti-Influenza B Type Antibody

Firstly, 1 ml of a 50 mM $KH_2PO_4$ buffer (pH 8.0) was added to 9 ml of a 50 nm-diameter gold colloid solution (EM. GC50, supplied by BBI), and the pH value of the gold colloid solution was thereby adjusted. Thereafter, 1 ml of an 80 µg/ml anti-influenza B type monoclonal antibody (MONOTOPE aby Influenza B Virus (nuclear) Purified 1131, supplied by ViroStat, Inc.) solution was added to the gold colloid solution, and the resulting mixture was stirred. After the mixture was allowed to stand for 10 minutes, 550 µl of an aqueous 1% polyethylene glycol (PEG Mw. 20,000, item No. 168-11285, supplied by Wako Pure Chemical Industries, Ltd.) solution was added to the mixture, and the resulting mixture was stirred. Thereafter, 1.1 ml of an aqueous 10% bovine serum albumin (BSA FractionV, item No. A-7906, supplied by Sigma-Aldrich Japan) solution was added to the mixture, and the resulting mixture was stirred. The solution having thus been obtained was subjected to centrifugal processing under the conditions of 8,000×g, 4° C., and 30 minutes (himacCF16RX, supplied by Hitachi, Ltd.). A supernatant liquid was then removed with approximately 1 ml being kept unremoved, and the gold colloid was then subjected to re-dispersing processing by use of an ultrasonic washing machine. Thereafter, the gold colloid was dispersed in 20 ml of a gold colloid storing liquid (20 mM Tris-HCl buffer (pH 8.2), 0.05% PEG (Mw. 20,000), 150 mM NaCl, 1% BSA, 0.1% $NaN_3$). The resulting dispersion was subjected to the centrifugal processing under the conditions of 8,000×g, 4° C., and 30 minutes. A supernatant liquid was then removed with approximately 1 ml being kept unremoved, and the gold colloid was then subjected to the re-dispersing processing by use of the ultrasonic washing machine. In this manner, an antibody-modified gold colloid (50 nm) solution was obtained.

(1-2) Preparation of Gold Colloid Antibody Supporting Pad (Labeling Substance Supporting Pad)

The gold colloid modified by the anti-influenza A type antibody and the gold colloid modified by the anti-influenza B type antibody, which gold colloids had been prepared as described under (1-1), were mixed together in a ratio of 1:1. The resulting solution was diluted with a gold colloid coating liquid (20 mM Tris-HCl buffer (pH 8.2), 0.05% PEG (Mw. 20,000), 5% sucrose) and water so as to obtain a diluted solution, whose optical density (OD) at a wavelength of 520 nm might be equal to 3.0. A glass fiber pad (Glass Fiber Conjugate Pad, supplied by Millipore Corporation) was cut into pads each having a size of 8 mm×150 mm, and the diluted solution described above was uniformly coated on each of the pads in a proportion of 0.8 ml per pad. The pads having thus been coated with the solution were dried overnight at reduced pressure, and gold colloid antibody supporting pads were thereby obtained.

(1-3) Preparation of Antibody-Fixed Membrane (Chromatographic Support)

With respect to a nitrocellulose membrane (provided with a plastic backing layer, HiFlow Plus HF120, supplied by Millipore Corporation) having been cut into a size of 25 mm×200 mm, fixation of antibodies was performed, and an antibody-fixed membrane was prepared in the manner described below. Specifically, a long side of the membrane was taken as a lower side. An anti-influenza A type monoclonal antibody (Anti-Influenza A SPTN-5 7307, supplied by Medix Biochemica Oy Ab) solution for fixation, which solution had been prepared so as to have a concentration of 1.5 mg/ml, was coated at a position, which was spaced by 7 mm from the lower side of the membrane, into a line-like pattern having a width of approximately 0.7 mm by use of an ink jet type coating machine (supplied by Bio Dot). Also, an anti-influenza B type monoclonal antibody (MONOTOPE aby Influenza B Virus (nuclear) Purified 1131, supplied by ViroStat, Inc.) solution for fixation, which solution had been prepared so as to have a concentration of 1.5 mg/ml, was coated at a position, which was spaced by 10 mm from the lower side of the membrane, into a line-like pattern having a width of approximately 0.7 mm. Further, an anti-mouse IgG antibody (Anti-Mouse IgG (H+L), rabbit F(ab')$_2$, item No. 566-70621, supplied by Wako Pure Chemical Industries, Ltd.) solution for control, which solution had been prepared so as to have a concentration of 0.5 mg/ml, was coated at a position, which was spaced by 13 mm from the lower side of the membrane, into a line-like pattern. The membrane having thus been coated with the solutions was dried at a temperature of 50° C. for 30 minutes by use of a warm-air type drying machine. Thereafter, 500 ml of a blocking liquid (a 50 mM boric acid buffer (pH 8.5) containing 0.5 wt % casein (milk-derived, item No. 030-01505, supplied by Wako Pure Chemical Industries, Ltd.)) was introduced into a tray, and the membrane was allowed to stand for 30 minutes in the blocking liquid. Thereafter, the membrane was transferred and dipped in 500 ml of a washing and stabilizing liquid (a 50 mM Tris-HCl (ph 7.5) buffer containing 0.5 wt % sucrose and a 0.05 wt % cholic acid sodium salt) having been introduced into a tray. The membrane was allowed to stand for 30 minutes in the washing and stabilizing liquid. The membrane was then taken out from the liquid and dried overnight at the room temperature. The thus obtained membrane was used as the antibody-fixed membrane (line coated).

(1-4) Preparation of Immunochromatographic Strip

The antibody-fixed membrane having been prepared in the manner described under (1-3) was adhered to a backing adhesive sheet (ARcare9020, supplied by NIPPN Techno Cluster). At this time, of the opposite long sides of the membrane, the long side close to the anti-influenza A type antibody line was taken as the lower side. The gold colloid antibody supporting pad, which had been prepared in the manner described under (1-2), was adhered to the lower side of the antibody-fixed membrane so as to overlap by approximately 2 mm upon the lower side of the antibody-fixed membrane. Also, a sample adding pad (a glass fiber pad having been cut into a size of 18 mm×150 mm (Glass Fiber Conjugate Pad, supplied by Millipore Corporation)) was adhered to the lower side of the gold colloid antibody supporting pad so as to overlap by approximately 4 mm upon the lower side of the gold colloid antibody supporting pad. Further, an absorbing pad (a cellulose glass film (CF6, supplied by Whatman) having been cut into a size of 80 mm×150 mm) was adhered to the upper side of the antibody-fixed membrane so as to overlap by approximately 5 mm upon the upper side of the antibody-fixed membrane. The member (immunochromatographic main body member) having thus been obtained from the overlapping adhesion processing was cut along lines parallel with the short side of the member by use of a guillotine type cutter (CM4000, supplied by NIPPN Techno Cluster), into strips each having a width of 15 mm, which width was taken along the long side of the member. In this manner, the immunochromatographic strip having a size of 15 mm×55 mm was prepared.

(1-5) Preparation of Silver Amplifying Solution (1-5-1) Preparation of Reducing Agent Solution Firstly, 23.6 ml of an aqueous iron nitrate solution having a concentration of 1 mol/l, which had been prepared by dissolving iron (III) nitrate nonahydrate (095-00995, supplied by Wako Pure Chemical Industries, Ltd.) in water, and 13.1 g of citric acid (038-16925, supplied by Wako Pure Chemical Industries, Ltd.) were dissolved in 290 g of water. After the dissolution was completed, 36 ml of nitric acid (10 wt %) was added to the resulting solution with stirring by use of a stirrer. Also, 60.8 g of iron (II)-ammonium sulfate hexahydrate (091-00855, supplied by Wako Pure Chemical Industries, Ltd.) was added. The thus obtained solution was used as the reducing agent solution.

(1-5-2) Preparation of Silver Ion Solution

Firstly, 8 ml of a silver nitrate solution (containing 10 g of silver nitrate) and 24 ml of an aqueous iron nitrate solution having a concentration of 1 mol/l were added to 66 g of water. Also, the resulting solution was mixed with a solution, which had been prepared previously by dissolving 5.9 ml of nitric acid (10 wt %), 0.1 g of dodecylamine (123-00246, supplied by Wako Pure Chemical Industries, Ltd.), and 0.1 g of a surface-active agent represented by the formula $C_9H_{19}$—$C_6H_4$—O—$(CH_2CH_2O)_{50}H$ in 47.6 g of water. The mixed solution having thus been obtained was used as the silver ion solution.

(1-6) Preparation of Dye Amplifying Solution

Dilution with an aqueous disodium hydrogenphosphate—NaOH buffer solution having been adjusted at a pH value of pH 9.3 was performed such that the quantity of 4-chloronaphthol might be equal to 0.6 mM, the quantity of hydrogen peroxide might be equal to 200 mM, and the quantity of the compound having the structure represented by the formula:

might be equal to 1.2 mM. A mixed solution was thus prepared such that the quantity of the mixed solution might be equal to 10 ml. At this time, in order for the dissolution of 4-chloronaphthol to be promoted, 100 μl of acetonitrile was dropped. The thus obtained mixed solution was used as the dye amplifying solution.

Example 1

(Device Setting)

Experiments were made by use of the immunochromatographic kit 10 as illustrated in FIG. 1. The immunochromatographic strip 1 having been prepared in the manner described under (1-4) was fitted to the first device part 11 shown in FIG. 1. Also, the liquid feeding insoluble support 2 and the absorbing insoluble support 3 were fitted to the second device part 12 shown in FIG. 1. The liquid feeding insoluble support 2 was constituted of a glass fiber pad (Glass Fiber Conjugate Pad, supplied by Millipore Corporation), which had been cut into a size of 18 mm×8 mm, and a backing adhesive sheet (ARcare9020, supplied by NIPPN Techno Cluster), which had been cut into a size of 13 mm×8 mm and had been adhered to the glass fiber pad described above. The absorbing insoluble support 3 was constituted of a cellulose membrane (CF6, supplied by Whatman), which had been cut into a size of 25 mm×8 mm, and a backing adhesive sheet (ARcare9020, supplied by NIPPN Techno Cluster), which had been cut into a size of 20 mm×8 mm and had been adhered to the cellulose membrane described above.

(Spotting and Development of Antigen Solution)

As the test body solution, Quick S-Influ A·B "Seiken" Negativity/Positivity Control (item No. 322968, supplied by DENKA SEIKEN Co., Ltd.) was used. The positivity control solution was diluted with a PBS buffer containing 1% by mass of BSA. With a commercially available immunochromatographic detection kit "Capllia Flu A·B" (supplied by Alfresa Pharma Corporation), the limit of the detection of Quick S-Influ AB "Seiken" was 1/40 for each of the A type and the B type. In Example 1, the positivity control solution was diluted to 1/200 with the PBS buffer containing 1% by mass of BSA, and the thus diluted positivity control solution was used as the test body solution. Specifically, 300 μl of the test body solution was spotted uniformly onto the sample adding pad 4 of the immunochromatographic strip 1 having been prepared in the manner described under (1-4), and the spotted test body solution was allowed to stand for 10 minutes.

(Washing)

After the antigen solution was developed for 10 minutes, 500 μl of the reducing agent solution having been prepared in the manner described under (1-5-1) was introduced into the liquid storing pot 13 of the first device part 11 as illustrated in FIG. 1. The second device part 12 was then closed so as to stand facing the first device part 11, and the edge of the liquid feeding insoluble support 2 was dipped in the reducing agent solution contained in the liquid storing pot 13. Also, the liquid feeding insoluble support 2 and the absorbing insoluble support 3 were fitted respectively from the opposite sides of the immunochromatographic strip 1 along the longitudinal direction of the immunochromatographic strip 1. The reducing agent solution was thus developed through the immunochromatographic strip 1 and was thus fed for three minutes. By the processing described above, the immunochromatographic strip 1 was dipped in the reducing agent solution, and the materials having not been adsorbed specifically to the immunochromatographic strip 1 were washed off.

(Signal Amplification by Amplifying Solution)

The silver ion solution having been prepared in the manner described under (1-5-2) was spotted from the spotting hole 15 of the second device part 12, and the signal of the gold colloid label having been adsorbed to the detection line was thus amplified for one minute. After the amplification, the immunochromatographic strip 1 was taken out and washed with water for three minutes.

Comparative Example 1

The operation up to the process for "washing" was performed in the same manner as that in Example 1. In the process for "signal amplification by amplifying solution," the residual liquid of the reducing agent solution contained in the liquid storing pot 13 of the first device part 11 was removed. Also, 500 μl of the silver ion solution having been prepared in the manner described under (1-5-2) was introduced into the empty liquid storing pot 13 and was fed from the liquid feeding insoluble support 2 toward the absorbing insoluble support 3. The signal of the gold colloid label having been adsorbed to the detection line was thus amplified for one minute. After the amplification, the immunochromatographic strip 1 was taken out and washed with water for three minutes.

Comparative Example 2

The operation up to the process for "washing" was performed in the same manner as that in Example 1. In the process for "signal amplification by amplifying solution," the residual liquid of the reducing agent solution contained in the liquid storing pot 13 of the first device part 11 was removed. Also, 500 μl of an amplifying solution, which had been prepared by mixing the silver ion solution having been prepared in the manner described under (1-5-2) and the reducing agent solution in a ratio of 1:4, was introduced into the empty liquid storing pot 13 and was fed from the liquid feeding insoluble support 2 toward the absorbing insoluble support 3. The signal of the gold colloid label having been adsorbed to the detection line was thus amplified for one minute. After the amplification, the immunochromatographic strip 1 was taken out and washed with water for three minutes.

<Evaluation>

The in immunochromatographic strip 1 after having been washed with water was subjected to imaging processing with a lumino image analyzer (LAS-4000, supplied by FUJIFILM Corporation) in a DigitizeEPI mode. With respect to an optical density of the detection line (ΔAbs. between a peak and a background), an absorbance ABS was calculated with the formula shown below:

$$ABS = \log(T_o/T_i)$$

wherein $T_o$ represents the output signal intensity at a position corresponding to an area of the immunochromatographic strip, at which the color formation has not occurred, and $T_i$ represents the output signal intensity at the detection line. Reference was made to a previously prepared calibration curve, and the concentration of the analyte contained in the test body solution was obtained.

Also, with visual inspection, nonuniformity in level of amplification was evaluated. Table 1 below shows the directions of the liquid feeding and the results of the evaluation. In Table 1, each of A, B, and C represents one of the directions of the liquid feeding as illustrated in FIGS. 4A, 4B, and 4C. Further, the density (mABS) shown in Table 1 represents milliABS (1,000×ABS).

TABLE 1

| | Test body solution + labeling antibody | Washing liquid (reducing agent solution) | Silver ion solution | Density (mABS) | Amplification nonuniformity |
|---|---|---|---|---|---|
| Example 1 | Direction A | Direction B | Direction C | 54 | Free from nonuniformity |
| Comparative Example 1 | Direction A | Direction B | Direction B | 0 | — |
| Comparative Example 2 | Direction A | Direction B | Direction B (reducing agent plus) | 32 | Much nonuniformity |

In Example 1, the signal of the detection line was amplified clearly and was easily confirmed with visual inspection. In Comparative Example 1, the reducing agent solution having wetted the antibody-fixed membrane was expelled by the silver ion solution, which was fed at the later stage, and the amplification did not proceed. In Comparative Example 2, in which the mixture of the reducing agent solution and the silver ion solution was caused to flow in the direction B, though the density was detected to be higher than in Comparative Example 1, much nonuniformity occurred in accordance with the amplified sites, and the results were not appropriate for use in practice.

Example 2

(Spotting and Development of Antigen Solution)

As the test body solution, Quick S-Influ A·B "Seiken" Negativity/Positivity Control (item No. 322968, supplied by DENKA SEIKEN Co., Ltd.) was used. The positivity control solution was diluted to 1/80 with the PBS buffer containing 1% by mass of BSA, and the thus diluted positivity control solution was used as the test body solution. The device setting was performed in the same manner as that in Example 1. Also, 500 μl of the test body solution was introduced into the liquid storing pot 13 of the first device part 11 as illustrated in FIG. 1. The second device part 12 was then closed so as to stand facing the first device part 11, and the edge of the liquid feeding insoluble support 2 was dipped in the test body solution contained in the liquid storing pot 13. Also, the liquid feeding insoluble support 2 and the absorbing insoluble support 3 were fitted respectively from the opposite sides of the immunochromatographic strip 1 along the longitudinal direction of the immunochromatographic strip 1. The test body solution was thus developed through the immunochromatographic strip 1 and was thus fed for 10 minutes.

(Development of Gold Colloid-Labeled Antibody)

Thereafter, 300 μl of a PBS buffer containing 1% by mass of BSA was spotted uniformly onto the sample adding pad 4 of the immunochromatographic strip 1 having been prepared in the manner described under (1-4). The gold colloid-labeled antibody having been fixed to the gold colloid antibody supporting pad was thus developed and was allowed to stand for 10 minutes.

(Signal Amplification by Dye Amplifying Solution)

The dye amplifying solution having been prepared in the manner described under (1-6) was spotted from the spotting hole 15 of the second device part 12, and the signal of the gold colloid label having been adsorbed to the detection line was thus amplified for one minute. After the amplification, the immunochromatographic strip 1 was taken out and washed with water for three minutes.

Examples 3, 4, and 5

An immunochromatographic strip was obtained in the same manner as that in Example 2, except that the extent of the dilution of the antigen solution was altered to 1/120, 1/140, or 1/160.

Comparative Example 3

An immunochromatographic strip was obtained in the same manner as that in Example 2, except that, in lieu of the process for "spotting and development of antigen solution" in Example 2, 300 μl of the test body solution having been prepared in the same manner as that in Example 2 was spotted uniformly onto the sample adding pad 4 of the immunochromatographic strip 1 having been prepared in the manner described under (1-4) and was allowed to stand for 20 minutes.

Comparative Examples 4, 5, and 6

An immunochromatographic strip was obtained in the same manner as that in Comparative Example 3, except that the extent of the dilution of the antigen solution was altered to 1/120, 1/140, or 1/160.

Evaluation was made in the same manner as that in Example 1 and Comparative Example 1. Table 2 below shows the directions of the liquid feeding and the results of the evaluation. In Table 2, as in Table 1, each of A, B, and C represents one of the directions of the liquid feeding as illustrated in FIGS. 4A, 4B, and 4C.

TABLE 2

| | Test body solution | Labeled antibody | Amplifying solution | Extent of dilution | Density (mABS) |
|---|---|---|---|---|---|
| Example 2 | Direction B | Direction A | Direction C | 1/80 | 119 |
| Example 3 | | | | 1/120 | 80 |

TABLE 2-continued

| | Test body solution | Labeled antibody | Amplifying solution | Extent of dilution | Density (mABS) |
|---|---|---|---|---|---|
| Example 4 | | | | 1/140 | 54 |
| Example 5 | | | | 1/160 | 30 |
| Comparative Example 3 | Direction A | Direction A | Direction C | 1/80 | 64 |
| Comparative Example 4 | | | | 1/120 | 15 |
| Comparative Example 5 | | | | 1/140 | — |
| Comparative Example 6 | | | | 1/160 | — |

As clear from Table 2, in each of Examples 2, 3, 4, and 5, wherein the directions of the liquid feeding of the test body solution, the labeled antibody solution, and the amplifying solution vary from one another, the analyte was detected in the cases of each extent of dilution. It was confirmed that, in cases where the directions of the liquid feeding of the test body solution and the labeled antibody solution vary from each other, the quantity of the label adsorbed to the detection site became large, the efficiency of the sandwich binding was enhanced, and therefore the detection was made with a high sensitivity. In each of Comparative Examples 3, 4, 5, and 6, wherein the directions of the liquid feeding of the test body solution and the labeled antibody solution coincided with each other, the detection was not possible in cases where the extent of the dilution of the antigen was equal to 1/140 or 1/160.

What is claimed is:

1. An assay method, comprising:
   i) preparing a plurality of different kinds of liquids, the plurality containing:
      a) a test body solution containing at least one analyte, and
      b) at least two different kinds of liquids selected from the group consisting of a washing liquid, an amplifying solution, and a detecting solution, and
   ii) feeding the plurality of different kinds of liquids to a detection site containing a specific binding substance for the analyte,
   wherein the directions of liquid feeding of the different kinds of liquids vary from one another, and the plurality of the different liquids are caused to intersect with one another at the detection site, and
   iii) detecting the presence or amount of analyte contained in the test body solution, and
   wherein a labeling substance signal, which is obtained from a labeling substance complex having been modified by a substance that has capability of binding with the analyte or the specific binding substance, is detected,
   wherein the detection site is formed on an insoluble support, and the liquid feeding is performed by capillary force arising through the insoluble support,
   wherein the plurality of different kinds of liquids includes the test body solution and the washing liquid, and at least one of the amplifying solution and the detecting solution,
   the test body solution is fed to the insoluble support (a) that is provided with the detection site,
   each of a liquid feeding insoluble support (b) for liquid feeding of the washing liquid and an absorbing insoluble support (c) for absorbing the washing liquid is brought into contact with the insoluble support (a) that is provided with the detection site,
   the washing liquid is fed to wash off substances other than the labeling substance which has been specifically bound with the detection site on the insoluble support (a) that is provided with the detection site, and
   the amplifying solution and the detecting solution are fed to the intersection site, at which the test body solution and the washing liquid intersect with each other,
   wherein the liquid feeding insoluble support (b) and the absorbing insoluble support (c) are brought into contact with the insoluble support (a) subsequent to the test body solution being fed to the insoluble support (a),
   wherein the insoluble support that is provided with the detection site has a strip-like shape, and the direction of the liquid feeding of the amplifying solution is normal and directly to a principal plane of the insoluble support that is provided with the detection site,
   wherein the labeling substance is constituted of a substance containing fine metal particles, and
   wherein the amplifying solution is a liquid containing silver ions.

2. The assay method as defined in claim 1 wherein a liquid containing a reducing agent for the silver ions contained in the amplifying solution is used as the washing liquid.

* * * * *